United States Patent

Groll et al.

[11] Patent Number: 5,298,218
[45] Date of Patent: Mar. 29, 1994

[54] PALLADIUM BASED ALLOY FOR DENTAL APPLICATIONS

[75] Inventors: Werner Groll, Alzenau; Doris Hathaway, Hanau; Bernd Kempf, Freigericht; Gernot Schöck, Bruchköbel, all of Fed. Rep. of Germany

[73] Assignee: Degussa Aktiengesellschaft, Frankfurt, Fed. Rep. of Germany

[21] Appl. No.: 939,477

[22] Filed: Sep. 4, 1992

[30] Foreign Application Priority Data

Sep. 6, 1991 [DE] Fed. Rep. of Germany ....... 4129592
Aug. 11, 1992 [DE] Fed. Rep. of Germany ....... 4226484

[51] Int. Cl.$^5$ ................................................. C22C 5/00
[52] U.S. Cl. ................................... 420/463; 420/432; 420/464
[58] Field of Search .................. 420/463, 464, 432

[56] References Cited

U.S. PATENT DOCUMENTS

| | | | |
|---|---|---|---|
| 4,319,877 | 3/1982 | Boyajian | 420/463 |
| 4,539,176 | 9/1985 | Cascone | 420/463 |
| 4,591,483 | 5/1986 | Nawaz | 420/463 |
| 4,619,810 | 10/1986 | Prasad | 420/463 |
| 5,174,954 | 12/1992 | Schaffer et al. | 420/463 |

FOREIGN PATENT DOCUMENTS

| | | |
|---|---|---|
| 3414575 | 7/1985 | Fed. Rep. of Germany . |
| 3830666 | 3/1990 | Fed. Rep. of Germany . |
| WO9008650 | 8/1990 | PCT Int'l Appl. . |

*Primary Examiner*—Upendra Roy
*Attorney, Agent, or Firm*—Beveridge, DeGrandi, Weilacher & Young

[57] ABSTRACT

Palladium based dental alloys do not show unaesthetic discolorations after ceramic firing if said alloys contain 66-85% by weight palladium, 1-20% by weight gold; 0-4% by weight silver; 0-4% by weight of at least one of platinum, iron and/or cobalt; 0.5-7% by weight of each of gallium, tin and indium, whereby the amount of said components total 9-14% by weight; 0-2% by weight germanium and/or zinc; and 0-1% by weight iridium, ruthenium and/or rhenium.

11 Claims, No Drawings

PALLADIUM BASED ALLOY FOR DENTAL APPLICATIONS

BACKGROUND AND INTRODUCTION

The present invention relates to the palladium alloys and use of such palladium alloys for the preparation of firmly fixed and removable dentures which are admixable with dental ceramics.

Dentures are predominantly prepared from corrosion resistant and biocompatible noble metal alloys according to the so-called wax melt process, whereby the cast object is often subsequently admixed (blended) with dental ceramics in order to obtain an appearance corresponding to natural teeth. In addition to a suitable strength, these alloys must possess special properties required for dental ceramics, e.g. expansion coefficient, melting interval, and adhesion between the ceramic and the alloy.

Alloys having a high gold content, e.g. alloys described in German patents 11 83 247 and 15 33 233, are particularly suitable for this purpose Because of the high price of gold, recent efforts have been made to find cheaper alternatives for alloys having a high gold content. In the field of noble metals, palladium seems to be a suitable substitute because palladium is relatively cheaper than gold, possesses a significantly lower density than gold, and shows a corrosion resistance and stability in the mouth similar to that of gold.

The hitherto developed fired alloys, which contain palladium as the main component, can be roughly divided into three groups:

The first group consists of gold-palladium alloys which are generally free of silver or have a very low silver content. Typical representatives of such alloys are described in German patents 34 06 712 and 29 44 755. However, these alloys are still relatively expensive due to the high gold content thereof.

The second group consists of palladium based alloys which are generally free of silver, e.g. alloys disclosed in German patents 33 16 595, 33 04 183, 35 22 523 and 32 47 398. The main alloy components of these alloys are copper and gallium. Further alloy components often used in these systems are tin, indium and cobalt As compared to fired alloys having a high gold content, the latter alloys are more difficult to be processed and are more sensitive to failures occurring during processing. These alloys are not easily solderable and take up carbon in the molten state, and for this reason they can be melted only in ceramic crucibles in order to avoid bubble formation in the fired ceramic mass. Moreover, all these alloys form oxides having a color from dark to black during the firing of the ceramic. Thus dark edges are formed in the marginal region of the blended mixture which adversely affect the aesthetic appearance of the dentures.

In U.S. Pat. No. 4,539,176, palladium alloys free of silver are disclosed which contain, in addition to palladium, 10–40% by weight gold, 3–8% by weight gallium, 0.5–10% by weight indium and/or tin, and 0.1–1.5% by weight ruthenium, iridium or rhenium. However, these alloys are unsuitable for the desired purposes.

The third group consists of palladium-silver alloys. The processing properties of these alloys are between those of alloys having a high gold content and palladium alloys free of silver. The typical composition of these alloys is disclosed in "Review of dental noble metal alloys and dental non-noble alloys in the German Federal Republic" (Übersicht uber die Dental-Edelmetallegierungen und Dental-Nichtedelmetallegierungen in der Bundesrepublik Deutschland), published by the "Research Institute of Dental Care" (Forschungsinstitut fur die zahnarztliche Versorgung), Jul. 1, 1986, pages 31–32. In addition to palladium and silver, these alloys predominantly contain tin, indium and zinc, and occasionally copper or gallium as further alloy components. The oxide color of these alloys is generally significantly lighter than that of silver-free palladium alloys. However, it is a drawback that these alloys give a yellow or yellowish-green discoloration to the ceramic blend during the firing process. The reason for this phenomenon is that silver migrates by diffusion or through the vapor phase into the ceramic. Several attempts were made to eliminate or at least reduce this tendency to discoloration of palladium-silver alloys by corresponding alloying conceptions.

In order to achieve this object, the addition of titanium in an order of magnitude of 0.1–0.5% is suggested by German patent 25 23 971, and the addition of 0.1–1% of silicon is suggested by U.S. Pat. No. 4,350,526. However, both of these solutions are accompanied by serious disadvantages from the point of view of dental processing properties. Both elements cause the embedding to adhere strongly to the casted objects and this makes the removal and finishing more difficult and slower.

Palladium forms with silicon intermetallic phases so that a strong embrittlement of the alloy and broken casting may occur. Moreover, both titanium and silicon are highly reactive to oxygen in the air, and for this reason the amount of these elements in the melt decreases relatively rapidly and this causes a reduction of the desired effect. This is particularly relevant when aged scrap material (cast channels, casting funnels) are applied.

According to German patent 39 05 987, palladium-silver alloys are made insensitive towards discoloration by adding germanium together with gallium and/or cobalt in a defined weight ratio. However, under unfavorable geometrical conditions and at the edges of the blend, ceramics sensitive towards discoloration may show signs of discoloration. Moreover, the market shows fundamental reservations against silver-containing palladium alloys even if the tendency to discoloration is reduced or completely eliminated.

In German patent 31 46 794, noble metal alloys suitable for firing of dental porcelain are disclosed. The alloys contain 0.05–1% by weight of one or more of the elements tantalum, tungsten and/or yttrium, in addition to 20–85% by weight palladium, 0–55% by weight of gold, 0–40% by weight of silver, 1–15% by weight tin and/or indium, and 0.1–3% by weight gallium, in order to improve the breaking elongation and casting brittleness. The disadvantage of tantalum and yttrium is that these metals are oxidized very easily and this results in slag formation in the crucible Tungsten forms a volatile oxide and this is disturbing during melting because of the formation of smoke and pores in the texture of the cast structure.

SUMMARY OF THE INVENTION

An object of the present invention is to provide a palladium alloy suitable for the preparation of dentures admixable with dental ceramics, which palladium alloy is free of copper, tantalum, tungsten, and yttrium, and shows no disturbing unaesthetic discolorations after firing of the ceramic.

According to the present invention, this and other objects are achieved by using a palladium alloy which contains 66-85% by weight palladium; 1-20% by weight gold; 0-4% by weight silver; 0-4% by weight of at least one of platinum, iron and/or cobalt and preferably 0.5-4% by weight platinum, iron and/or cobalt; 0.5-7% by weight of each of gallium, tin and indium, whereby the amount of these components totals 9-14% by weight; 0-2% by weight germanium and/or zinc; and 0-1% by weight of iridium, ruthenium and/or rhenium.

DETAILED DESCRIPTION OF THE INVENTION

It is preferred to use palladium alloys which contain 66-85% by weight palladium; 2-20% by weight gold; 1-3.5% by weight iron; 3.1-7% by weight gallium, 1.5-7% by weight tin and indium each, whereby the amount of the components gallium, tin and indium totals 9-14% by weight; 0-4% by weight platinum; 0-2% by weight germanium and/or zinc; and 0-1% by weight iridium, ruthenium and/or rhenium. These silver-free alloys form a particularly light oxide if they contain iron but do not contain cobalt.

The palladium alloy being free of copper, tantalum, tungsten, and yttrium is defined as containing less than 100 ppm of said metals; naturally occurring impurities are not excluded.

Those palladium alloys are also advantageous which contain, in addition to the above-mentioned alloy components, as an obligatory feature, 0.5-2% by weight germanium and/or zinc. These additives lead to a reduction of optionally formed porosities.

According to a further preferable embodiment of the present invention, there are provided palladium alloys which contain 66-85% by weight palladium; 10-20% by weight gold; 0.5-4% by weight platinum; 3.1-7% by weight gallium, 1.5-7% by weight tin and indium each, with the proviso that the amount of gallium, tin and indium totals between 9 and 14% by weight. These palladium alloys can contain additionally 0-2% by weight germanium and/or zinc and 0-1% by weight of iridium, rhodium and/or rhenium.

Palladium alloys, which contain no or only a small amount of silver, are generally suitable for processing in dental technics only if they contain further non-noble metals which decrease the melting interval and increase the thermal expansion coefficient (TEC). These alloys can be molded with conventional casting equipment and blended with generally used dental ceramics known in the art only if the above-mentioned non-noble metal additives are present.

The addition of the above non-noble metal components generally cause the oxide layer of the alloys to become very dark and the well-known aesthetical problems occur. Surprisingly, it has been found that significantly lighter oxide layers are formed if the non-noble metals gallium, tin and indium are simultaneously used in an amount of 1.5-7% by weight each, whereby the amount of these non-noble metals in the alloy totals 9-14% by weight. The elements silver, gold, platinum, germanium, zinc, iron, and cobalt serve to adjust the physical properties of the alloy (e.g. strength, hardness, capability of being cast, thermal expansion coefficient, and melting interval).

Ruthenium, rhenium and/or iridium are incorporated into the alloy in an amount of 0-1% by weight in the form of fine particles. Experiments carried out with blend ceramics of various types have shown that in the case of the above alloy concept even a small portion of silver (up to about 4% by weight) surprisingly does not cause any discoloration. Since silver containing palladium alloys are treated by many dental technicians with serious reservations, it is a further object of the present invention to prepare absolutely silver-free palladium alloys with light oxide. At first the removal of silver leads to a considerable darkening of the oxide and an increase of the melting temperature; however, it has been surprisingly found that an increase of the gallium content to at least 3.1% by weight causes a decrease of the melting interval.

On alloying iron in an amount of at least 1% by weight a very light oxide can be obtained. Moreover, the above amount of iron leads to a desirable decrease of the melting interval and to an increase of the thermal expansion coefficient; accordingly the decrease of the thermal expansion coefficient due to the removal of silver can be re-compensated. On the other hand, the iron content should not be too high because this can cause strong oxide formation when casting with open flame; the upper limit for iron content is 4%. The above oxidation phenomena lead also to the formation of blistery porous casting cones. This phenomenon can be significantly decreased by adding a small amount (0.5 to 2%) of germanium and/or zinc.

The iron and cobalt content of the alloy leads on molding to brown and blue discolorations, respectively, of the embedding mass on the surfaces contacted with the liquid metal. This discoloration does not affect the quality and processing of the dental technical cast. Nevertheless, such discolorations are treated with reservations. The removal of iron and cobalt can, however, lead to unacceptable high melting intervals and too low thermal expansion coefficients. It has been surprisingly found, however, that by using gold in an amount of at least 10% by weight and gallium in an amount of at least 3.1 % by weight, palladium alloys with light oxide and good dental technical processing properties are obtained.

Iron and cobalt free alloys having a relatively high gold content particularly tend to have somewhat lower thermal expansion coefficient values and a coarsely granular structure (texture).

Although the above hardness values still fall into the hardness interval of fired alloys having a high gold content, due to the widespread use of palladium-based alloys nowadays generally high hardness values are preferred. In this respect the alloying of platinum proved to be particularly useful. The addition of platinum results in an increase of hardness, whereby no augmentation of the melting interval takes place if the platinum content is increased at the expense of the palladium content. Moreover, platinum affects the fineness of structure (texture) in a preferable way so that the amount of the agent improving the fineness of the particles need not to be increased. Thus platinum exhibits a double positive effect on the capability of the alloys of being polished. On the one hand, in this case the high hardness is advantageous while on the other hand, as a result of the effect of platinum, the amount of the agent improving the fineness of the particles can be maintained at a low level so that the capability of being polished is not affected in an adverse manner by hard agents improving the fineness of the particles.

In Table 1 the composition of some representatives of the alloys of the present invention is disclosed. In Table 2 the properties are set forth and the color of the oxides of alloys of the present invention are compared to that of known copper-containing palladium alloys and palladium-silver alloys, respectively (described in DE 33 16 595). Substitution of ruthenium with iridium and/or rhenium in similar amount in the alloys of Table i will lead to comparable results.

TABLE 1

| Alloy | Content (% by weight) | | | | | | | | | | | |
|---|---|---|---|---|---|---|---|---|---|---|---|---|
| | Pd | Ag | Au | Pt | Fe | Co | Ga | Sn | In | Zn | Ge | Ru |
| 1 | 79.5 | — | 5.5 | — | 3 | — | 5 | 4 | 2 | 0.5 | — | 0.5 |
| 2 | 77 | 2 | 5.5 | — | — | 3 | 4 | 4 | 4 | — | — | 0.5 |
| 3 | 79 | 1 | 5.5 | — | — | 2 | 4 | 4 | 4 | — | — | 0.5 |
| 4 | 76 | 3 | 5.5 | — | — | 2 | 4 | 4 | 4 | 1 | — | 0.5 |
| 5 | 74.5 | 2 | 9 | — | — | 2 | 4 | 4 | 4 | — | — | 0.5 |
| 6 | 81.5 | — | 2.5 | — | 3 | — | 4 | 4 | 4 | — | 0.5 | 0.5 |
| 7 | 71 | — | 15 | 1.4 | — | — | 6 | 4 | 2 | — | 0.1 | 0.5 |
| 8 | 79.5 | 2 | 2.5 | — | — | 3 | 4 | 4 | 4 | — | 0.5 | 0.5 |
| 9 | 66.5 | — | 17.5 | 3 | — | 1 | 6.5 | 4 | 1.5 | 0.5 | — | 0.5 |

TABLE 2

| Alloys | Melting Interval (°C.) | Hardness after Casting (HV5) | Hardness after Firing (MV5) | Comparison of the colors of oxides | |
|---|---|---|---|---|---|
| | | | | Cu-containing Palladium alloys | Ag-containing Palladium alloys |
| 1 | 1298–1209 | 252 | 247 | + | + |
| 2 | 1317–1194 | 226 | 220 | + | + |
| 3 | 1331–1231 | 203 | 210 | + | 0 |
| 4 | 1302–1223 | 217 | 222 | + | + |
| 5 | 1328–1233 | 234 | 230 | + | 0 |
| 6 | 1321–1218 | 254 | 239 | + | 0 |
| 7 | 1295–1190 | 261 | 250 | + | 0 |
| 8 | 1312–1221 | 230 | 221 | + | + |
| 9 | 1286–1182 | 262 | 253 | + | 0 |

+ = of equal quality
0 = of equal quality

The color of the oxide was determined by direct comparison with conventional silver-free and copper-containing palladium based alloys and with palladium-silver alloys. On preparing the samples, conventional dental technical processing steps were carried out by imitating conventional conditions as exactly as possible. After dental technical casting each crown was separately removed, treated with aluminum oxide (110 μm particle size) and subsequently subjected to a simulated ceramic firing whereby the samples were subjected to all of the treating steps from the oxide firing up to the polishing firing without applying a ceramic. Finally the oxide colors thus obtained were evaluated by direct comparison with two standard samples at daylight by two persons.

The following evaluation grades are disclosed: oxide color identical, lighter or darker, respectively, than that of the comparative sample (Table 2 designated as "0", "+" or "−"). All alloys of the present invention show a lighter oxide than the conventional silver-free, copper-containing palladium alloys and for this reason in this column only the designation "+" appears. On comparing with palladium-silver alloys both lighter and darker oxide colors were found.

The present invention further relates to dentures comprising a dental ceramic known in the art and the palladium alloy described above. The dentures are prepared by methods known in the art. The underlying denture formed from the alloy is coated with the ceramic which is fired onto the alloy thereby caused the ceramic to adhere to the alloy. Thus the alloy is capped with the ceramic.

The present invention also relates to a veneered dental prothesis comprising a ceramic material veneer and a dental prothesis, wherein the ceramic material veneer is known in the art and the dental prothesis comprises the palladium alloy described above. The veneered dental prothesis are prepared by methods known in the art. The underlying dental prothesis is coated with the ceramic material veneer which is fired onto the alloy thereby causing the ceramic material veneer to adhere to the alloy. Thus the alloy is capped with the ceramic material veneer.

Further variations and modifications of the foregoing will be apparent to those skilled in the art and such variations and modifications are attended to be encompassed by the claims that are appended hereto.

German Priority Application P 41 29 592.7 filed on Sep. 6, 1991 and P 42 26 484.7 filed on Aug. 11, 1992 are relied on and incorporated by reference.

What is claimed:

1. A palladium alloy free of copper, tantalum, tungsten and yttrium, for the preparation of dentures admixable with dental ceramics, said alloy comprising 66–85% by weight palladium, 1–20 % by weight gold, 0–4% by weight silver, 0–4% by weight of each of platinum, iron and/or cobalt; 0.5–7% by weight of each of gallium, tin and indium, whereby the amount of said gallium, tin and indium totals 9–14% by weight; 0–2% by weight of germanium and/or zinc, and 0–1% by weight of iridium, ruthenium and/or rhenium.

2. The palladium alloy according to claim 1, comprising 0.5–4% by weight of platinum, iron and/or cobalt.

3. The palladium alloy according to claim 1, comprising 66–85% by weight palladium, 2–20% by weight of gold, 1–3.5% by weight iron, 3.1–17% by weight gallium, 1.5–7% by weight of tin and indium each, whereby the amount of gallium, tin and indium totals 9–14% by weight, 0–4% by weight platinum, 0–2% by weight germanium and/or zinc, and 0–1% by weight iridium, ruthenium and/or rhenium.

4. The palladium alloy according to claim 1, comprising 66–85% by weight palladium, 10–20% by weight gold, 0.5–4% by weight platinum, 2.1–7% by weight of gallium, 1.5–7% by weight tin and indium each, whereby the amount of gallium, tin and indium totals 9–14% by weight, 0–2% by weight germanium and/or zinc, and 0–1% by weight iridium, ruthenium and/or rhenum.

5. The palladium alloy according to claim 1, wherein said alloy contains no silver.

6. The palladium alloy according to claim 1, comprising 0.5–2% by weight germanium and/or zinc.

7. The palladium alloy according to claim 1, comprising 0% by weight of silver and at least 3.1% by weight of gallium.

8. The palladium alloy according to claim 1, comprising 0% by weight of silver, 0.5–2% by weight germanium and/or zinc, and at least 1% by weight of iron.

9. The palladium alloy according to claim 1, comprising at least 10% by weight of gold and at least 3.1% by weight of gallium and where iron and/or cobalt is present.

10. The palladium alloy according to claim 2, comprising 66–85% by weight palladium, 2–20% by weight gold, 0.5–3.5% by weight platinum, 1–3.5% by weight iron, 3.1–7% by weight gallium, 1.5–7% by weight tin and indium each, whereby the amount of gallium, tin and indium totals 9–14% by weight, 0.5–2% by weight germanium and/or zinc, and 0–1% by weight iridium, ruthenium and/or rhenium.

11. The palladium alloy according to claim 3, wherein said alloy contains no cobalt.

* * * * *